(12) United States Patent
Dorai et al.

(10) Patent No.: US 6,355,846 B1
(45) Date of Patent: Mar. 12, 2002

(54) NARROWING OF POLY (TETRAMETHYLENE ETHER) GLYCOL

(75) Inventors: Suri Narayan Dorai, Owings Mills, MD (US); Richard Edward Ernst, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/690,650

(22) Filed: Oct. 17, 2000

(51) Int. Cl.[7] .............................................. C07C 43/11
(52) U.S. Cl. ....................................... 568/617; 568/619
(58) Field of Search .................................. 568/617, 619

(56) References Cited

U.S. PATENT DOCUMENTS

| | | | |
|---|---|---|---|
| 3,925,484 A | 12/1975 | Baker | 260/615 B |
| 4,115,408 A | 9/1978 | Baker | 260/346.11 |
| 4,933,503 A | 6/1990 | Mueller | 568/621 |
| 5,282,929 A | 2/1994 | Dorai et al. | 203/91 |

*Primary Examiner*—Sreeni Padmanabhan
*Assistant Examiner*—Sikarl A. Witherspoon

(57) ABSTRACT

A process for producing a poly(tetramethylene ether) glycol (PTMEG) or copolymer having a narrowed molecular weight ratio of 1.9 to 2.07 and a dispersity of 1.2 to 1.65 from a starting PTMEG or copolymer with a broader molecular weight distribution having a dispersity of 1.9 to 2.3 and a molecular weight ratio of 2.3 to 2.6 is provided by feeding the PTMEG or copolymer and an effective amount of an inert solvent to a stripping apparatus and stripping at a temperature of 150 to 220 degrees C. and a pressure of 0.5 to 5 mm of mercury.

11 Claims, 2 Drawing Sheets

NARROWING OF POLY (TETRAMETHYLENE ETHER) GLYCOL

BACKGROUND OF THE INVENTION

1. Field of the Invention

The present invention relates to a process for narrowing the dispersity and molecular weight distribution of poly (tetramethylene ether) glycol by stripping out lower weight fractions or oligomers at a low pressure and elevated temperature using an inert solvent

2. Description of Related Art

Poly (tetramethylene ether) glycol (PTMEG) is a commodity in the chemical industry, widely used to form segmented copolymers with polyfunctional urethanes and polyesters. It is typically made by the polymerization of tetrahydrofuran (THF) using a strong acid catalyst such as fluorosulfonic acid and then quenching the product with water. The resulting PTMEG polymer contains molecules of varying chain lengths, with a molecular weight distribution that is quite broad, non-Gaussian and skewed toward higher molecular weight fractions. If the chain length variation is too great, and in particular if the polymer contains too high a percentage of short chain molecules or oligomers, it can have a harmful effect on the properties of the end product.

Most commercial plants use fluorosulfonic acid as the catalyst. When using this catalyst, the polymer produced in the polymerization reaction is believed to be the sulfate ester, which is hydrolyzed with water to obtain higher, more economic yields of the polyol product. Unreacted THF is removed from the resultant aqueous polymer dispersion by conventional steam stripping. The acidic aqueous dispersion of impure PTMEG is then subjected to washing with water. The purpose of the washing is twofold: (1) to remove the sulfuric acid and hydrofluoric acid from the polymeric dispersion, and (2) to remove the low molecular weight PTMEG fraction from the polymer by taking advantage of the high solubility of the low molecular weight species in water.

PTMEG copolymers are typically made by a similar process in which anhydrous THF is copolymerized with alkylene oxides, for example ethylene oxide or propylene oxide. In certain copolymers, up to about 20% by weight of the THF can be replaced by 3-methyl tetrahydrofuran. Additionally, small amounts of other monomers, i.e., below about 10% by weight of the total monomers, can be present to modify product characteristics.

In a conventional fluorosulfonic acid-catalyzed THF polymerization system, the low molecular weight PTMEG fraction is washed out of the polymer. Generally, a substantial amount of aqueous acidic effluent results from the PTMEG washing. U.S. Pat. No. 4,115,408 provides a process for recovering the dissolved PTMEG fractions by converting it to THF by a high temperature depolymerization process.

U.S. Pat. No. 3,925,484 to Baker (assigned to E.I. du Pont de Nemours and Company, hereafter DuPont) discloses a process for producing PTMEG having a narrow molecular weight distribution of about 1.3 to 1.7 by partially depolymerizing the PTMEG at a temperature from about 120 to 150 degrees C. The lower molecular weight fractions in this case are converted most rapidly to tetrahydrofuran (THF) by the partial depolymerizing process and so removed from the polymer. Even though the process produces PTMEG with a narrow molecular weight distribution, the conversion of substantial amounts of polymer to a lower value THF restricts the use of this technique.

U.S. Pat. No. 4,933,503 to Mueller discloses a process for narrowing the molecular weight distribution of PTMEG and of copolymers of PTMEG and alkylene oxides by distilling off the low molecular weight fractions at pressures of less than 0.3 mbar at 200 to 260 degrees C, and then mixing the distillation residue with a specified three-component solvent system which forms three separate phases each containing a narrow weight distribution polymer.

BRIEF SUMMARY OF THE INVENTION

The present invention is a process for narrowing the molecular weight distribution and dispersity of poly (tetramethylene ether) glycol or copolymer comprising the steps of:

feeding poly(tetramethylene ether) glycol or copolymers thereof having a molecular weight ratio of 2.3 to 2.6 and a dispersity of 1.9 to 2.3 and an effective amount of an inert solvent to a stripping apparatus which has one or more separation stages wherein the stripping is conducted at a temperature of 150 to 220 degrees C and a pressure of 0.5 to 5 mm of mercury;

recovering a vaporized overhead mixture of inert solvent and a low molecular weight fraction of the poly (tetramethylene ether) glycol polymer or copolymer; and recovering from the bottom of the stripping apparatus an unevaporated poly(tetramethylene ether) glycol polymer or copolymer having a reduced molecular weight ratio of 1.9 to 2.07 and a dispersity of 1.2 to 1.8.

BRIEF DESCRIPTION OF THE DRAWING(S)

DETAILED DESCRIPTION OF THE INVENTION

Figure 1:
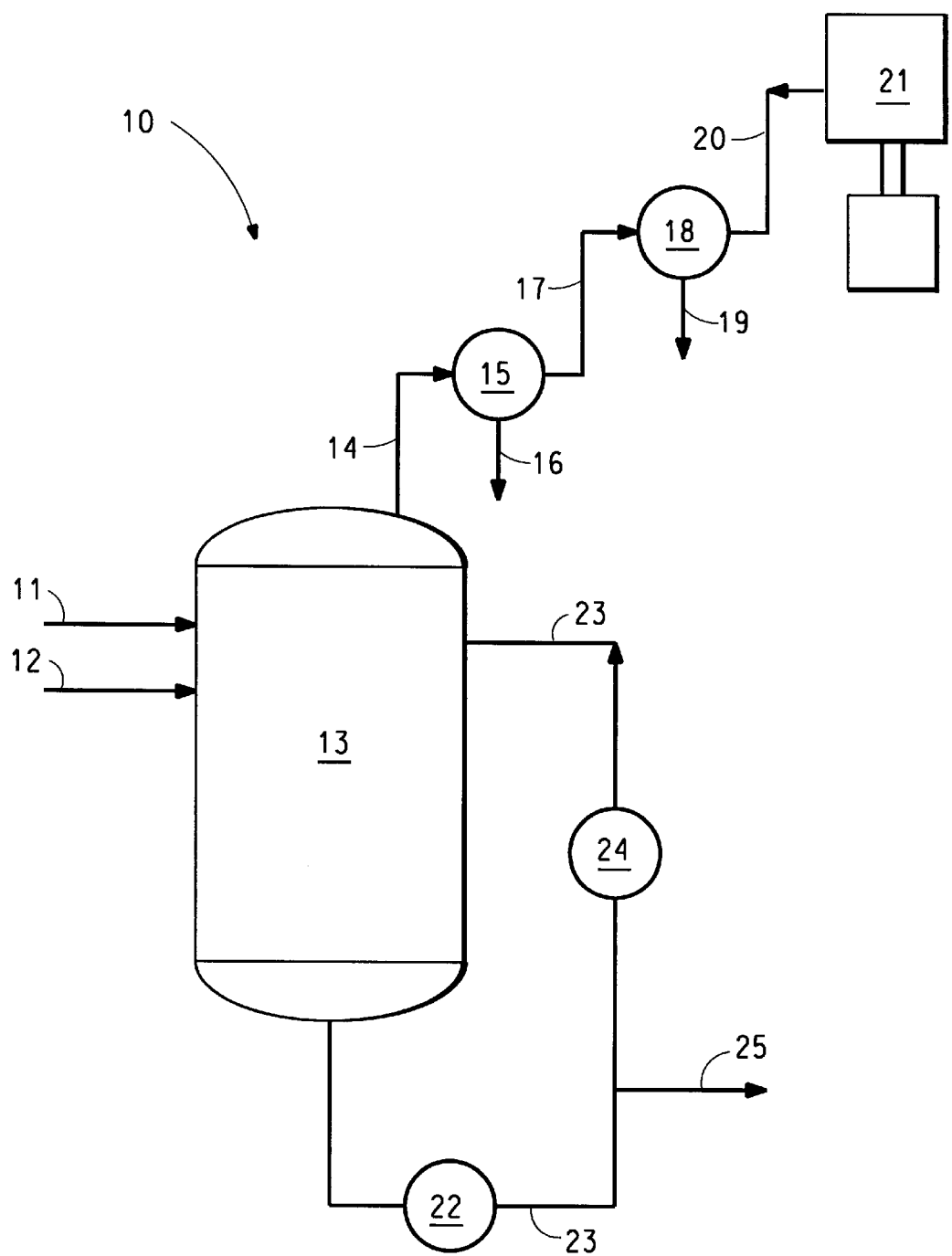
FIG. 1 depicts the process demonstrating concurrent flow.

Certain terms, which are typical molecular weight distribution parameters and whose meanings are set out below, are used herein to describe the invention.

The uniformity of the molecular weight distribution of a polymer is usually measured by its dispersity: the ratio of its weight average molecular weight ($M_w$) to the number average molecular weight ($M_n$). A high ratio indicates a wide spread of molecular weights for the polymer, and a low ratio nearing 1 indicates a narrower molecular weight distribution of the polymer.

The number average molecular weight is defined as:

$M_n$=(Sum of $W_i$ for all i Values) divided by (Sum of all ($W_i/M_i$))

where:

$W_i$ is the weight of the "i" species oligomer, and, $M_i$ is the molecular weight of the "i" species oligomer.

Typically $M_n$ is determined by end group analysis by titration.

The weight average molecular weight is defined as: $M_w$ =(Sum of ($W_iM_i$) for all "i" values) divided by (Sum of $W_i$) for all "i" values. Typically $M_w$ is determined by gel permeation chromatography (GPC) or liquid chromatography.

Another measure of the breadth of molecular weight distribution is the Molecular Weight Ratio or MWR. It is related to the melt viscosity of the polymer as follows:

$$MWR = 1160\,(n)^{0.493}/M_n$$

Where n is the melt viscosity of the polymer in poise.

The present invention relates to a process for preparing a narrow molecular weight distribution PTMEG polymer or copolymer by using either a batch or continuous stripping process for removal of low molecular weight species in a single or multiple stage system by adding an inert solvent and stripping out the low molecular weight species at low pressure and elevated temperature. The initial molecular weight distribution immediately after polymerization typically corresponds to a dispersity of 1.9 to 2.3, whereas the desirable molecular weight dispersity is 1.2 to 1.8. The initial Molecular Weight Ratio immediately after polymerization typically corresponds to an MWR of 2.3 to 2.6, whereas the desirable MWR is 1.9 to 2.1.

In the context of this invention, an inert solvent means an alcohol, diol (glycol) or hydrocarbon that does not react with the PTMEG or copolymer under process conditions, and that has a boiling point and freezing point consistent with the chosen temperature and pressure of the stripping and condensation apparatus. That is, the choice of temperature, pressure and inert solvent are such that the inert solvent exists in vapor form during the stripping operation. The preferred inert solvent is 1,4-butane diol. This material is a starting material for the THF and PTMEG processes and thus does not introduce an impurity into the PTMEG or copolymer system.

In the process of this invention, PTMEG or copolymer having a molecular weight ratio of 2.3 to 2.6 and a dispersity of 1.9 to 2.3 and an effective amount of an inert solvent are fed to a stripping apparatus. The stripping is conducted at a temperature of 150 to 220 degrees C and a pressure of 0.5 to 5 mm of mercury. A vaporized mixture of inert solvent and a low molecular weight fraction of the PTMEG or copolymer is recovered overhead, and an unevaporated PTMEG or copolymer having a reduced molecular weight ratio of 1.9 to 2.1 and a dispersity of 1.2 to 1.8 is recovered from the bottom of the stripping apparatus In the above process, the liquid PTMEG or copolymer and the vaporized or liquid inert solvent can be fed to the stripping apparatus either countercurrently or concurrently, and either batchwise or continuously. The overhead mixture of inert solvent and low molecular weight fraction of the PTMEG or copolymer can be condensed at a temperature and pressure which condenses a low molecular weight PTMEG fraction substantially free of the recovered inert solvent. Optionally, the condenser temperature and pressure can be chosen so as to condense both the low molecular weight PTMEG fraction and the inert solvent, which are then separated by distillation or other means. The recovered inert solvent can be returned to the stripping apparatus for reuse.

The stripping apparatus can be a vessel, an open column, a packed or sieve-tray column, or other means for carrying out a stripping operation. The stripping apparatus can have one or more separation stages. For simplicity, a single-stage vessel or open column is preferred.

DETAILED DESCRIPTION OF THE DRAWINGS

One method of setting up the stripping operation is illustrated in FIG. 1, in which case the stripping operation is carried out by using apparatus 10. Preheated PTMEG and 1,4-butane diol (1,4-BDO) are co-fed through lines 11 and 12, respectively to a single-stage stripping unit 13. The term T250 refers to the low molecular weight PTMEG fraction to be removed from the feed PTMEG. The overhead vapors are first sent through line 14 to a condenser 15 for condensing the T250,which is removed through line 16. The vapors then are sent through line 17 to a condenser 18 for recovering the BDO. The BDO is removed through line 18 and can be recycled. The remaining non-condensables are sent through line 20 to a vacuum pump 21. The stripper is heated by circulating a bottoms stream through a heat exchanger 20 and returning it to the stripper via line 23. A side-stream from the bottoms pump is removed through line 25 as narrowed PTMEG product.

Figure 2:
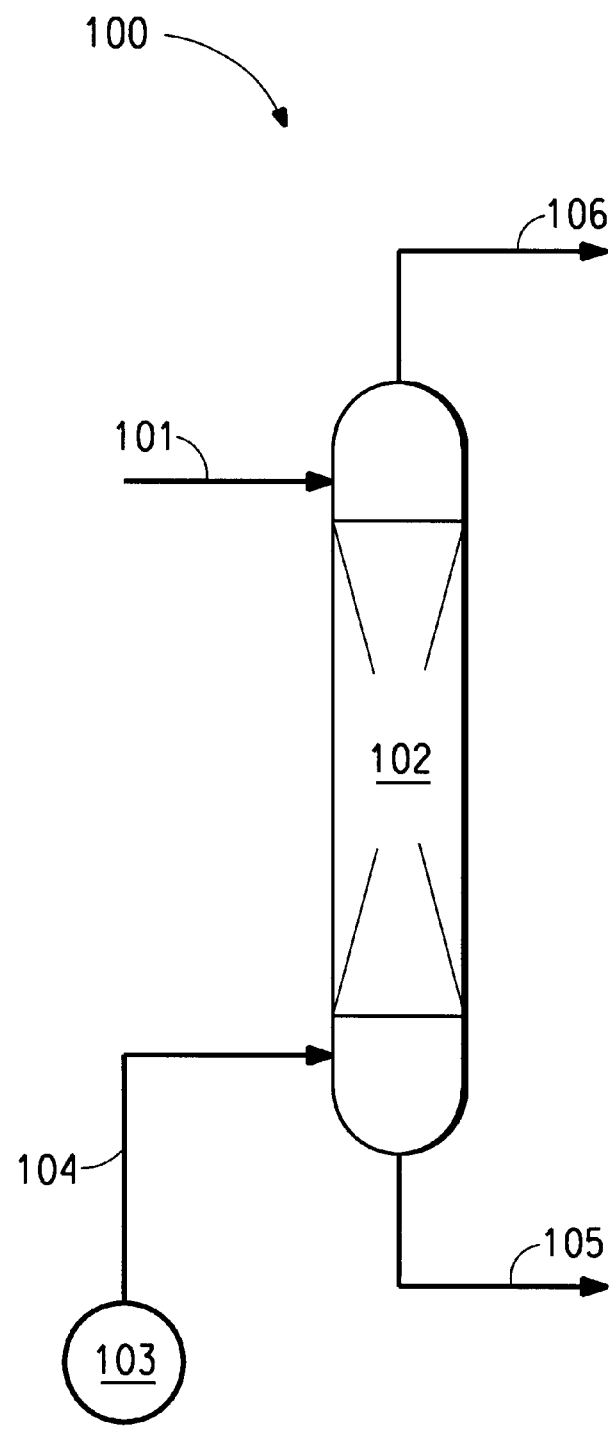
FIG. 2 depicts the process demonstrating countercurrent flow.

A second method of setting up the stripping operation is illustrated in FIG. 2, in which case stripping is carried out by using apparatus 100. The PTMEG is introduced through line 101 to the top of a multi-stage stripping column 102 in countercurrent flow to 1,4-butane diol vapors. In this case the butane diol is heated and vaporized in vaporizer 103 before entering the bottom portion of stripping column 102 through line 104. The narrowed PTMEG product is removed from the bottom of the stripping apparatus through line 105. The overhead vapor stream is passed through line 106 and then treated the same as depicted in FIG. 1.

The stripping operation is carried out at in the temperature range of 150 to 220 degrees C. Lower temperatures are undesirable because an uneconomically high vacuum would be required for effective operation. Higher temperatures are undesirable because they can adversely affect product quality. The desired stripping temperature is most easily achieved by controlling the overall heat balance of the combined PTMEG component and inert solvent feeds. The PTMEG component and inert solvent can be fed at the same or different temperatures, and at the same or different locations of the stripper. The inert solvent can be fed to the stripping apparatus as a vapor. Alternatively, the solvent can be fed as a pressurized liquid if the overall heat balance and operating pressure require it to be a vapor when inside the stripping apparatus.

The stripping operation can be carried out without a significant temperature difference between the top and bottom of the stripping apparatus. Optionally, the apparatus can be designed to have a temperature at the top of the apparatus lower than at the bottom, in effect adding a distillation effect to the stripping effect. This temperature difference can be achieved as can be understood by reference to FIG. 2 by feeding the liquid PTMEG at the top of a stripping column at a lower temperature than the vaporized inert solvent entering at the bottom of the column.

The stripping operation is carried out at a pressure of 0.5 to 5 mm of mercury. A lower pressure is uneconomical because of the high cost of the vacuum system required. A higher pressure is ineffective in carrying out the desired stripping operation without the need for higher temperatures, which can adversely affect product quality.

An inert gas, such as nitrogen, can be fed to the bottom of the stripping operation. However, the stripping operation is preferably carried out without the addition of an inert gas because it adds considerably to the volume of gases that must be removed by the system's vacuum pumps.

The effective amount of inert solvent to be added depends on a number of factors. For example, a higher amount of inert solvent is required with a higher pressure in the stripping apparatus or with a lower temperature. The greater the number of separation stages in the stripping apparatus, the lower the amount of inert solvent required. The greater the reduction in PTMEG dispersity required, the greater the amount of inert solvent required. And of course, the amount of inert solvent required (on a weight ratio basis) will vary with the molecular weight of the inert solvent chosen. Once the above independent factors are selected or fixed, one skilled in the art can readily determine the effective amount of inert solvent required by a few experiments.

The following examples are intended to illustrate the invention, but not to limit its scope.

EXAMPLES

Example 1

Using the apparatus and PTMEG of Example 2, 150 g of unnarrowed PTMEG was placed in the reactor, the pressure was reduced to 1.1 mm Hg, the reactor was heated to 180 C, and 1,4-butane diol (1,4-BDO) feed was started at a 0.6 g/min flow rate. The 1,4-BDO was fed as a liquid at room temperature, but it was heated and vaporized as it passed down the sparger tube, such that it entered the reactor through the glass frit as a vapor. This flow was continued for 65 minutes until 40 g of 1,4-BDO had been passed through into the reactor. The reactor temperature and pressure were maintained at 175 C and 1.1 mm Hg throughout the test, and these conditions were maintained for an additional 18 minutes after stopping the 1,4-BDO feed. Samples of the PTMEG left in the pot, and of the PTMEG/BDO stripped out overhead (50.0 g total, including the 1,4-BDO) were analyzed by GPC for molecular weight and dispersity. The PTMEG left in the pot had a Mn of 1003 and dispersity of 1.637, PTMEG/BDO and the PTMEG stripped out overhead had a Mn of 238 and dispersity of 1.020. This experiment shows that butane diol effectively removes the low molecular weight fraction of PTMEG from the unnarrowed PTMEG. Since the 1,4-BDO can be readily removed from the non-condensable gases by condensation, the high cost of a vacuum system that would be required for using nitrogen is eliminated.

Similarly, this example used a vacuum of only 1.1 mm Hg (1.5 mbar), compared to the high vacuum of 0.001 mm to 0.01 mbar preferred for the short-path distillation evaporators of U.S. Pat. No. 5,282,929. Thus, this invention replaces the above complex short-path distillation units with a simple stripping system, eliminating most of the cost of the short-path system.

Example 2

In this experiment, nitrogen was used as the stripping agent to test its effectiveness and the stripping concept. The equipment consisted of a 500 ml round-bottomed flask, equipped with heating mantles (both bottom and top), a thermometer, a fritted-glass sparger (near the bottom), a magnetic stirrer, and a condenser. Runs were made by charging about 150 g PTMEG having a broad molecular weight range (unnarrowed) to the flask, and as described below, reducing the pressure to the desired level, heating to the desired temperature, and then starting the stripping fluid at the desired flow rate. The exiting gas was condensed with a cold water condenser, and the collection flask was cooled with dry ice. The nitrogen was passed through a preheater before entering the sparger.

The starting unnarrowed PTMEG used for this work had a $M_n$ of 862, and a dispersity of 1.741 (both determined by GPC). Then 155 g of this unnarrowed PTMEG was placed in the reactor, the pressure was reduced to 0.7 mm Hg, the reactor was heated to 180 C, and the nitrogen flow was started at 42 sccm. This nitrogen flow was continued for 26 minutes, during which time the reactor temperature slowly rose to 240 C and the pressure was maintained at 0.7 mm Hg. At this point very little additional polymer was detected leaving the condenser. The system was shut down, and samples of the PTMEG left in the pot and samples of the material stripped out overhead (collected 14.1 g), were analyzed by GPC for molecular weight distribution and dispersity. The material left in the pot had a Mn of 1050 and dispersity of 1.513, and the material stripped out overhead had a $M_n$ of 336 and dispersity of 1.073.

This laboratory example illustrated the feasibility of stripping with an inert gas as a method to improve the dispersity of PTMEG. However, it also demonstrated that the size of the vacuum system needed on a plant scale to handle the large amount of nitrogen required would make this process very difficult to perform on a commercial scale.

We claim:

1. A process for narrowing the molecular weight distribution and dispersity of poly(tetramethylene ether) glycol or copolymer comprising the steps of:

feeding poly(tetramethylene ether) glycol or copolymer thereof having a molecular weight ratio of 2.3 to 2.6 and a dispersity of 1.7 to 2.3 and an effective amount of an inert solvent to a stripping apparatus which has one or more separation stages wherein the stripping is conducted at a temperature of 150 to 220 degrees C. and a pressure of 0.5 to 5 mm of mercury;

recovering a vaporized overhead mixture of inert solvent and a low molecular weight fraction of the poly (tetramethylene ether) glycol polymer or copolymer; and recovering from the bottom of the stripping apparatus an unevaporated poly(tetramethylene ether) glycol polymer or copolymer having a reduced molecular weight ratio of 1.9 to 2.07 and a dispersity of 1.2 to 1.65.

2. The process of claim 1, wherein the poly (tetramethylene ether) glycol polymer or copolymer and the inert solvent are fed to the stripping apparatus concurrently.

3. The process of claim 1, wherein the poly (tetramethylene ether) glycol polymer or copolymer and the inert vapor solvent are fed to the stripping apparatus countercurrently.

4. The process of claim 1, wherein the inert solvent is selected from the group consisting of alcohol, glycol and hydrocarbon having a boiling point of 150 to 220 degrees C. at a pressure of 0.5 to 5 mm of mercury.

5. The process of claim 4, wherein the inert solvent is 1,4-butane diol.

6. The process of any one of claims 1 to 5, wherein the overhead mixture of inert solvent and low molecular weight fraction of the poly(tetramethylene ether) glycol polymer or copolymer is condensed at a temperature and pressure that produces a poly(tetramethylene ether) glycol polymer or copolymer substantially free of the recovered inert solvent.

7. The process of claim 6, wherein the copolymer comprises repeat units derived from one or more units of monomers selected from the group consisting of tetrahydrofuran, 3-methyl tetrahydrofuran and alkylene oxides.

8. The process of claim 7, wherein the alkylene oxide is selected from the group consisting of ethylene oxide and propylene oxide.

9. The process of claim 6, wherein the recovered inert solvent is returned to the stripping apparatus.

10. The process of claim 6, wherein an inert gas is fed into the bottom of the stripping apparatus.

11. The process of claim 10, wherein the inert gas is nitrogen.

* * * * *